(12) United States Patent
Oyler (10) Patent No.: US 9,003,695 B2
(45) Date of Patent: Apr. 14, 2015

(54) CONTROLLED GROWTH ENVIRONMENTS FOR ALGAE CULTIVATION

(75) Inventor: James R. Oyler, Salt Lake City, UT (US)

(73) Assignee: Genifuel Corporation, Salt Lake City, UT (US)

( * ) Notice: Subject to any disclaimer, the term of this patent is extended or adjusted under 35 U.S.C. 154(b) by 2127 days.

(21) Appl. No.: 11/966,885

(22) Filed: Dec. 28, 2007

(65) Prior Publication Data

US 2008/0155890 A1  Jul. 3, 2008

Related U.S. Application Data

(60) Provisional application No. 60/877,774, filed on Dec. 29, 2006.

(51) Int. Cl.
*A01G 33/00* (2006.01)
*A01H 13/00* (2006.01)
*C12M 1/00* (2006.01)
*C12M 1/34* (2006.01)
*C12N 1/12* (2006.01)

(52) U.S. Cl.
CPC ............... *A01H 13/00* (2013.01); *A01G 33/00* (2013.01); *C12M 21/02* (2013.01); *C12M 23/18* (2013.01); *C12M 31/08* (2013.01); *C12M 41/10* (2013.01); *C12M 41/40* (2013.01); *C12N 1/12* (2013.01)

(58) Field of Classification Search
CPC ...... A01G 33/00; C12M 21/02; C12M 23/06; C12M 41/10; C12M 41/40; C12N 1/12
USPC .............. 47/1.4; 119/200, 233, 263; 210/602, 210/747
See application file for complete search history.

(56) References Cited

U.S. PATENT DOCUMENTS

| 2,383,579 | A | 8/1945 | Allen et al. |
| 2,383,632 | A | 8/1945 | Trent |
| 3,650,068 | A | 3/1972 | Meyer et al. |
| 3,958,364 | A | 5/1976 | Schenck et al. |
| 4,236,349 | A | 12/1980 | Ramus |
| 4,368,691 | A | 1/1983 | Brune |

(Continued)

FOREIGN PATENT DOCUMENTS

| WO | WO 2007/013899 | 2/2007 |
| WO | 2007/089151 | 12/2007 |
| WO | WO 2008/008262 | 1/2008 |

OTHER PUBLICATIONS

Ulf Schuchardt, et al, Transesterification of Vegetable Oils: a Review, J. Braz. Chem. Soc., vol. 9, No. 1, 199-210, 1998.

(Continued)

*Primary Examiner* — Monica Williams
(74) *Attorney, Agent, or Firm* — Thorpe North & Western, LLP (57) ABSTRACT

A method for cultivating algae can include providing a body of water in a substantially enclosed system. The enclosed system can have a length of channel and a cover. The method can optionally include circulating the body of water through the enclosed system under positive pressure conditions. The positive pressure should prevent ingress of any external atmosphere or material. Further, the method can include cultivating the algae in the body of water at conditions which promote growth. Likewise, a system for cultivating algae can include a channel with a cover, water in the channel, and a pump to introduce positive pressure into the system.

22 Claims, 2 Drawing Sheets

(56) References Cited

U.S. PATENT DOCUMENTS

| | | | |
|---|---|---|---|
| 4,658,757 A | | 4/1987 | Cook |
| 4,910,912 A | | 3/1990 | Lowrey, III |
| 5,216,976 A | * | 6/1993 | Marinkovich ............... 119/200 |
| 5,417,824 A | | 5/1995 | Greenbaum |
| 5,578,472 A | | 11/1996 | Ueda et al. |
| 5,766,474 A | * | 6/1998 | Smith et al. .................. 210/602 |
| 5,776,344 A | | 7/1998 | McCarty et al. |
| 5,846,423 A | | 12/1998 | Jensen |
| 5,846,816 A | | 12/1998 | Forth |
| 6,233,870 B1 | * | 5/2001 | Horibata ....................... 47/62 R |
| 6,237,284 B1 | | 5/2001 | Erickson |
| 6,579,714 B1 | | 6/2003 | Hirabayashi et al. |
| 6,790,669 B1 | | 9/2004 | Pfeiffer |
| 6,827,036 B2 | * | 12/2004 | Connolly ..................... 119/208 |
| 6,858,430 B1 | | 2/2005 | Reddy et al. |
| 6,986,323 B2 | | 1/2006 | Ayers |
| 7,112,229 B2 | | 9/2006 | Khalil et al. |
| 7,135,308 B1 | | 11/2006 | Bush et al. |
| 2002/0023296 A1 | * | 2/2002 | Bussey et al. .................... 4/498 |
| 2002/0034817 A1 | | 3/2002 | Henry et al. |
| 2002/0072109 A1 | | 6/2002 | Bayless et al. |
| 2004/0049976 A1 | | 3/2004 | Maffei |
| 2005/0112735 A1 | | 5/2005 | Zappe et al. |
| 2005/0234278 A1 | | 10/2005 | Van Egmond et al. |
| 2006/0094089 A1 | | 5/2006 | Barclay |
| 2006/0186020 A1 | | 8/2006 | Gomes |
| 2006/0286205 A1 | | 12/2006 | Fichtali et al. |
| 2007/0260102 A1 | | 11/2007 | Duarte Santiago et al. |

OTHER PUBLICATIONS

John Sheehan et al, A Look Back at the U.S. Department of Energy's Aquatic Species Program—Biodiesel from Algae, Close-Out Report, National Renewable Energy Laboratory/U.S. Department of Energy, NREL/TP-580-24190, Jul. 1998.

Alexei Barrionuevo, Archer Daniels to Look Beyond Corn for Fuel Sources, New York Times, Nov. 9, 2005, www.nytimes.com/2006/11/09/business/09adm.html?ei=5088&en=0e5de3501bbb3.

Michael Briggs, Widescale Biodiesel Production from Algae, University of New Hampshire, Physics Dept, UNH Biodiesel Group, www.unh.edu/p2/biodiesel/article_alge.html, revised Aug. 2004, p. 1-11.

J. Van Gerpen et al, Biodiesel Production Technology, Subcontractor Report, National Renewable Energy Laboratory/U.S. Dept. of Energy, Office of Energy Efficiency and Renewable Energy, Contract No. DE-AC36-99-GO10337, NREL/SR-510-36244, Jul. 2004, p. 1-106.

Xiaoling Miao et al, Biodiesel Production from Heterotrophic Microalgal Oil, Department of Biologial Sciences and Biotechnology, Tsinghua University, Beiging 100084, PR China, Biosource Technology 97 (2006) p. 841-846.

Charlotte Schubert, Can biofuels finally take center stage?, Nature Biotechnology vol. 24 No. 7 Jul. 2006, p. 777-784, www.nature.com/naturebiotechnology.

Charles L. Peterson et al, Toxicolgy, Biodegradability and Environmental Benefits of Biodiesel, White Paper, accessed Mar. 28, 2008, http://www.biodiesel.org/resources/reportsdatabase/reports/mar/19940101_mar-002.pdf.

Ralph P. Overend, Hydrogen from Algae, National Renewable Energy Laboratory, ASES-renewable Hydrogen Forum, Apr. 10-11, 2003, World Resources Institute Washington, D.C.

Brent Erickson, Cellulosic Ethanol and Biorefineries: The Future is Now, Powerpoint, accessed Mar. 28, 2008, http://www.bio.org/ind/biofuel/EthanolfromCelluloseFutureisNow.pdf.

U.S. Appl. No. 11/966,909, Genifuel Corporation; filed Dec. 28, 2007.

U.S. Appl. No. 60/877,786, Genifuel Corporation; filed Dec. 29, 2006.

U.S. Appl. No. 11/966,898, Genifuel Corporation; filed Dec. 28, 2007.

J. Van Gerpen et al., Biodiesel Production Technology Aug. 2002-Jan. 2004, NREL/SR-510-36244 Chpt 8 p. 56-65 http://www.nrel.gov/docs/fy04osti/36244.pdf.

Greenfuel Technologies Corporation: Emissions to Biofuels Technology; www.greenfuelonline.com/technology.htm p. 1-2, as accessed on Nov. 27, 2006.

Oilagae.com-Oil from Algae! Biodiesel from Algae Oil—Info, Resources, News & Links, www.oilgae.com, p. 1-4, as accessed on Nov. 27, 2006.

Algae Oil Extraction, From Oilgae.com-Oil & Biodiesel from Algae, www.oilgae.com/algae/oil/extract/extract.html, p. 1-4, as accessed on Nov. 27, 2006.

Roger A. Korus et al, Transesterification Process to Manufacture Ethyl Ester of Rape Oil, White Paper, accessed Mar. 28, 2008, http://journeytoforever.org/biofuel_library/EthylEsterofRapeOil.pdf.

Thomas F. Riesing, PH D., Cultivating Algae for Liquid Fuel Production, http://oakhavenpc.org/cultivating_algae.htm p. 1-7, as accessed on Nov. 14, 2007.

Cultivation of Algae Strains for Biodiesel, From Oilgae.com—Oil from Algae (So what's the Oilgae story?); www.oilgae.com/algae/oil/biod/cult/cult.html p. 1-8, as accessed on Nov. 14, 2007.

Soap Bubble Unsulated Solar Greenhouse; www.solarbubblebuild.com; accessed from website Nov. 14, 2007; 4 pgs.

Thomas F. Riesing, Ph.D.; Cultivating Algae for Liquid Fuel Production; http://oakhavenpc.or/cultivating_algae.htm; accessed from website Nov. 14, 2007; 7 pgs.

U.S. Appl. No. 13/026,767, filed Feb. 14, 2011; James R. Oyler; notice of allowance dated Jan. 8, 2013.

U.S. Appl. No. 13/026,767, filed Feb. 14, 2011; James R. Oyler; office action dated Jul. 10, 2012.

U.S. Appl. No. 13/932,955, filed Jul. 1, 2013; James R. Oyler; office action dated Feb. 10, 2014.

* cited by examiner

CONTROLLED GROWTH ENVIRONMENTS FOR ALGAE CULTIVATION

RELATED APPLICATIONS

This application claims the benefit of U.S. Provisional Patent Application No. 60/877,774, filed on Dec. 29, 2006, which is incorporated by reference herein in its entirety.

FIELD OF THE INVENTION

The present invention relates generally to enclosed environments for encouraging growth of algae. Accordingly, the present invention involves the chemical, biological, and material science fields.

BACKGROUND OF THE INVENTION

The group of organisms referred to as algae is one of the most prolific and widespread on earth. Over 150,000 species of algae are currently known, and it is certain that more remain to be discovered. Of this large number of species, only a relative handful has been studied in detail. All that is known about the majority of algae species is their name and basic identifying characteristics and qualities. In fact, there is even some uncertainty about how to classify all the different algae species in the overall taxonomy of life.

What is known is that algae (including plant-like forms of many different sizes and colors, diatoms, and cyanobacteria) constitute one of the most important types of life on earth, responsible for most of our atmosphere as well as forming the basis of the food chain for many other forms of life. Entire ecosystems have evolved around algae or symbiotically with algae, and the algal environment includes food sources, predators, viruses, and many other environmental elements that we typically associate with higher forms of life.

Despite the extent and importance of algae, direct human use has been limited. Algae are grown or harvested as food, especially in Asia and often in the form of "seaweed." They are also widely used to produce various ingredients such as colorants and food additives. Algae are used in the treatment of municipal waste streams, and in industrial processes to concentrate and remove heavy metal contamination. Fossil forms known as diatomaceous earth are used as a filtration medium and for other applications.

An application of algae which has begun to emerge in recent years is as a source of fuel. It is known that algae can produce oil, starch, and gas, which can be used in production of diesel fuel, alcohol (e.g. ethanol), and hydrogen or methane gas.

While other biological materials can also yield these fuels, what distinguishes algae are their high productivity and theoretical low cost. Algae can grow from 10 to 100 times as fast as other forms of plants, and can grow well under a wide range of temperature, water quality, and nutrient conditions. Algae can also be highly prolific in their production of desired oils or starches, in some cases producing as much as 60% of their own weight in these forms. Moreover, algae achieve all this with the most basic of inputs, needing only sunlight, water, air, and simple nutrients.

Despite the clear potential benefits of algae as a fuel source, actually achieving this potential has proved frustrating and difficult, for a number of reasons. For example, we do not know enough about what species among the many species of algae are the best for optimum growth under specific conditions. Further, little is known about how to grow algae in a selectable, controlled and repeatable way, or how to encourage high productivity in forming fuel-precursor materials such as oil or starch.

SUMMARY OF THE INVENTION

Despite the above drawbacks and limitations, the potential uses of algae in production of valuable fuels and chemicals are sufficient to merit further investigation and development. Accordingly, the present invention provides a multi-stage method of cultivating algae which can include providing a body of water in a substantially enclosed system having a length of channel, and two covers. The two covers can have different translucence, meaning one permits greater amounts of light through the cover compared to the other cover. Algae can be cultivated in such system within the body of water and under conditions sufficient to promote algae growth and oil production. In one aspect, the growth can include a light growth stage and a dark growth stage. In a further aspect, the dark growth stage can be a function of the cover having the lower translucence being oriented over the body of water.

Likewise, a system for cultivating algae can include a channel with a cover system that substantially closes the channel to an outside environment and forms a protected growth volume. The cover system can be designed to selectively adjust amounts of light allowed to enter the protected growth volume. The system can further include a body of water including an algae contained in the channel, and a gas pump configured to introduce a positive pressure into the protected growth volume.

There has thus been outlined, rather broadly, various features of the invention so that the detailed description thereof that follows may be better understood, and so that the present contribution to the art may be better appreciated. Other features of the present invention will become clearer from the following detailed description of the invention, taken with the accompanying claims, or may be learned by the practice of the invention.

BRIEF DESCRIPTION OF THE DRAWINGS

The drawings will be described further in connection with the following detailed description. Further, these drawings are not necessarily to scale and are by way of illustration only such that dimensions and geometries can vary from those illustrated.

DETAILED DESCRIPTION OF THE INVENTION

Definitions

In describing and claiming the present invention, the following terminology will be used in accordance with the definitions set forth below.

The singular forms "a," "an," and "the" include plural referents unless the context clearly dictates otherwise. Thus, for example, reference to "an algae" includes reference to one or more of such algae, and reference to "the cover" includes reference to one or more of such covers.

As used herein, the term "about" is used to provide flexibility to a numerical range endpoint by providing that a given value may be "a little above" or "a little below" the endpoint, while the exact degree of a "little" will depend on the context as understood by those skilled in the art.

As used herein, "channel" refers to any fluid guide that is capable of transporting fluids along a desired path. Channels can include troughs, pipes, trenches, conduits, or other similar structures.

As used herein, "gas pump" refers to any pump device or system that can introduce gaseous substances into a system. As such, gas pump includes compressor, fan, and blower, and all can be configured to introduce a positive pressure into an enclosed system.

The term "translucent" is meant to include material that allows light radiation through. As such, translucent includes transparent materials. Opaque materials may be suitable for use as a portion or entirety of the cover if dark growth conditions are desired. As such, one material having a greater translucence than another would allow a greater amount of light radiation through.

As used herein, the term "substantially" refers to the complete or nearly complete extent or degree of an action, characteristic, property, state, structure, item, or result. For example, an object that is "substantially" enclosed would mean that the object is either completely enclosed or so nearly completely enclosed so as to prevent ingress of materials to the same practicable extent. The exact allowable degree of deviation from absolute completeness may, in some cases, depend on the specific context. However, generally speaking, the nearness of completion will be so as to have the same overall result as if absolute and total completion were obtained. The use of "substantially" is equally applicable when used in a negative connotation to refer to the complete or near complete lack of an action, characteristic, property, state, structure, item, or result. For example, a composition that is "substantially free of" particles would either completely lack particles, or so nearly completely lack particles that the effect would be the same as if it completely lacked particles. In other words, a composition that is "substantially free of" an ingredient or element may still actually contain such item as long as there is no measurable effect on properties of interest thereof.

As used herein, a plurality of items, structural elements, compositional elements, and/or materials may be presented in a common list for convenience. However, these lists should be construed as though each member of the list is individually identified as a separate and unique member. Thus, no individual member of such list should be construed as a de facto equivalent of any other member of the same list solely based on their presentation in a common group without indications to the contrary.

Concentrations, amounts, and other numerical data may be expressed or presented herein in a range format. It is to be understood that such a range format is used merely for convenience and brevity and thus should be interpreted flexibly to include not only the numerical values explicitly recited as the limits of the range, but also to include all the individual numerical values or sub-ranges encompassed within that range as if each numerical value and sub-range is explicitly recited. As an illustration, a numerical range of "about 1 to about 5" should be interpreted to include not only the explicitly recited values of about 1 to about 5, but also include individual values and sub-ranges within the indicated range. Thus, included in this numerical range are individual values such as 2, 3, and 4 and sub-ranges such as from 1-3, from 2-4, and from 3-5, etc., as well as 1, 2, 3, 4, and 5, individually.

This same principle applies to ranges reciting only one numerical value as a minimum or a maximum. Furthermore, such an interpretation should apply regardless of the breadth of the range or the characteristics being described.

The Invention

The present invention provides a method for cultivating algae. The method includes providing a body of water in a substantially enclosed system. The enclosed system has a length of channel and a cover situated over at least a portion of the length of channel. The body of water can be circulated through the enclosed system under positive pressure conditions. The positive pressure conditions can be such that ingress of external atmosphere and/or materials is prevented or at least substantially prevented. Further included in the method is cultivating the algae within the body of water and under conditions sufficient to promote growth of the algae.

Similarly, a method of cultivating algae can include providing a body of water in a substantially enclosed system including a length of channel and at least two covers over the length of channel. A first cover can have a greater translucence than a second cover. The first cover and optionally the second cover can contribute to the substantially enclosed system. The method can further include cultivating an alga within the body of water under at least two growth stages under conditions sufficient to promote growth of algae.

Many variables can be considered in selecting conditions sufficient to promote algae growth. Non-limiting examples of variables include temperature, salinity, pH, circulation rate, amount of nutrients, type of nutrients, amount and source of light radiation, amount and type of algae, amount of carbon dioxide, and configuration of enclosed system. Conditions can be selected and maintained to promote selective growth of one or more desired strains of algae over one or more undesired strains of algae. In one embodiment, the body of water may be heated to a temperature for optimized growth of the desired algae. In another embodiment, the body of water may be cooled to a temperature for optimized growth of the desired algae. The necessity for either heating or cooling can be a function of the climate and location of the growth environment, e.g. New Mexico versus Wyoming or summer versus winter. The temperature for optimum growth may be determined by the desired algae growth. In one aspect, the water may be maintained at a temperature of from about 10° C. to about 70° C. In a further aspect, the temperature may be maintained from about 20° C. to about 40° C.

In one aspect, the enclosed system can include perforations in the cover. Such perforations can be located at strategic points along the channel, and/or can be located at evenly spaced intervals along the channel. Including perforations in the enclosed system can assist in maintaining a desired pressure within the system and can additionally prevent blowouts or failures in the system by controlled pressure release.

Water can be circulated through the system at any rate and in any configuration that is conducive to algae growth. In a detailed aspect, the body of water can be circulated at a flow rate of from about 15 cm/s to about 30 cm/s. The depth of the water can affect algae growth as light radiation is limited at greater depths. Therefore, the depth of the body of water, in one aspect, can be from about 10 cm to about 30 cm in the channel. The channel can be a variety of configurations, lengths, and widths. In one aspect, the channel width can be from about 1 m to about 3 m. Alternatively, the system can be configured as a non-continuous channel, and the water can be aerated and mixed by the release of gas at or near the bottom of the channel bed.

Since algae require nutrients and carbon dioxide for optimum growth, such materials can be introduced into the substantially enclosed system. In one embodiment, carbon dioxide can be injected into the body of water. Likewise, one or more nutrients can be injected into the body of water.

The method can further include harvesting the algae. Such harvesting can be complete harvesting of the algae in the system (i.e. a batch process), or can be conducted by selecting a portion of the algae in the system (i.e. a continuous, or semi-continuous process).

Likewise, a system for cultivating algae can include a channel with a cover, water including algae contained in the channel, and a gas pump. The channel and cover can be substantially closed to the environment and can form a protected growth volume. The channel and cover are substantially translucent on at least a portion thereof sufficient to allow light to enter the protected growth volume. The gas pump can introduce a positive pressure into the protected growth volume. Further, the pump can be configured to introduce a gas into the water.

Further, a system for cultivating algae can include a cover system that substantially closes the channel to an outside environment and forms a protected growth volume. The cover system can be designed to selectively adjust amounts of light allowed to enter the protected growth volume. The system can additionally include a body of water including an algae contained in the channel, and a gas pump configured to introduce a positive pressure into the protected growth volume.

A system can optionally include a reflecting surface on a portion of an inner wall of the channel. Such reflecting surface can be oriented to redirect, or reflect, light through the protected growth volume. Through use of a reflecting surface, the light energy introduced into the enclosed system can be more efficiently utilized for algae growth.

Multiple designs for the cover and/or cover system are contemplated. In one embodiment, the cover system can include a first cover and a second cover, where the first cover has a greater translucence than the second cover. Such covers can be utilized individually, as different areas of the growth volume, or can be used together, where the second cover is used to cover both the channel and the first cover whenever processing conditions merit such arrangement. In one embodiment, the cover can be flexible. In a further embodiment, the flexible cover can be plastic. One configuration includes a loose-fitting flexible cover that stretches across the channel and is optionally attached to the channel structure. Under positive pressure, the loose-fitting cover creates a dome. Regardless of the flexibility of the cover, the cover or covers can span the width of one or more channels.

The channel can preferably be formed in the earth, although other configurations are possible. Channels can take many forms. In one embodiment, the channel can be a plurality of folded switch-backs, e.g. serpentine. Various materials can be used in the construction of channels. In one aspect, the channel can be substantially composed of concrete, plastic, fiberglass, or composites or combinations of these materials.

The systems and methods presented herein provide for the efficient growth of algae in a controlled environment. Within the controlled environment, the conditions can be controlled so as to encourage and sustain growth of the algae. The enclosed environment can also allow for production of selective species of algae. The efficient growth of algae requires that the growing conditions be carefully controlled to protect the desired species, to provide optimum growth conditions, and to encourage optimum production of lipids, starches, or other desired substances by the algae.

One of the most fundamental problems in algaculture (the controlled growing of algae) is the selection and control of the species actually growing. Algae are truly ubiquitous, and can be found almost everywhere on earth, above the earth, and under the earth. Any open body of water will soon be colonized with algae (or already has algae in it). Further, the open body of water will probably have many different kinds of algae. As conditions change, such as with seasonal changes or changes in the water, the mix of species will likewise adapt and change. For example, the dominant species may be quite different in winter than in summer.

Since different species can be quite different in their growth characteristics as well as their ability to produce desired "crops" of oil or starch, this constant adaptation and change is not likely to be useful for the algae farmer. It is analogous to trying to grow a crop of wheat without knowing what variety of wheat is growing from day to day or being able to control predators, disease, or competitors such as weeds (all of which exist in algae just as in wheat). Moreover, if desired types of algae are developed either by natural selection or genetic engineering, other types of wild or volunteer algae could displace the selected algae types quite quickly.

It is possible that a "super species" of algae could be developed with sufficient effort: one that is highly productive for the desired crop of oil or starch, that is dominant in its environment, and that remains productive and dominant in a wide range of conditions. However, such a goal not only seems unlikely, but is certainly not here today. Therefore, the apparent solution is to provide tight control over the growth environment by means of a growth system that controls the key variables-species, temperature, salinity, pH, nutrients, and other growing conditions. In addition, the system can use the lowest possible amount of water, nutrients, and other inputs.

Further, the growth system can be designed to be economical, or inexpensive to construct and operate, while remaining highly productive. Any high-volume production of products from algae (or any other biological source) will face strong competition from more traditional sources and processes, which set the standard for economical pricing.

To date, most efforts to grow algae have been done in open ponds, and none have yet succeeded for more than a short time, though for short periods some very interesting results have been achieved. A new and improved approach is needed.

The systems of the present invention can be substantially closed ones. Closed systems can be used for a number of reasons, such as: to prevent invasion by unwanted species or predators, to allow control of temperature, to prevent unnecessary evaporation of water, to hold desired nutrients and gases in the system, and to prevent contamination from other environmental variables.

Figure 1:
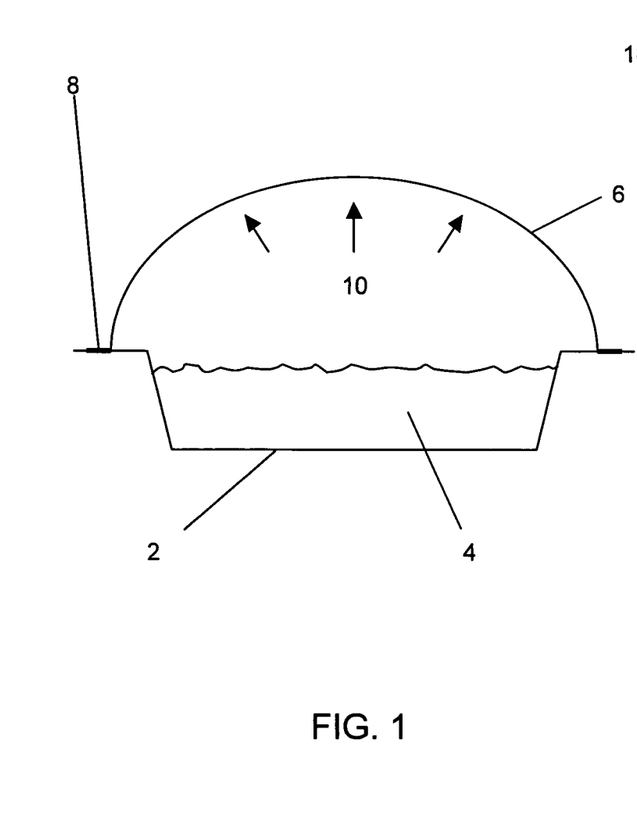
FIG. 1 is a cross-section view of a channel with a cover in accordance with one embodiment of the present invention.
Figure 2:
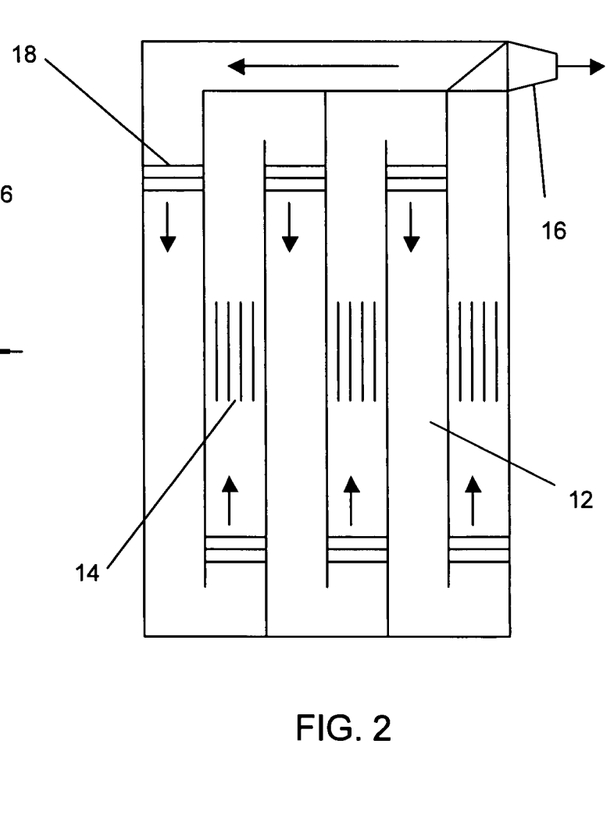
FIG. 2 is an overhead view of a channel system in accordance with another embodiment of the present invention.

A closed system can be achieved economically by using a simple channel and a cover in accordance with the present invention. An example of a channel and cover is illustrated in FIG. 1. The channel 2 can be formed of any material and in any location that allows for the creation of a substantially enclosed system. Water including algae 4 can be contained in the channel. The cover 6 can be situated over the channel and sealed to the channel at a sealing point 8. A gas pump can be configured to introduce a positive pressure 10 into the protected growth volume, which can optionally be sufficient to cause the cover to inflate. In one preferred aspect, the channel can be formed in the earth, although suitable channels can also be formed above the earth. Channels can take the form of many designs, which allow for the circulation of water and/or protection of water containing algae from surrounding environment. Along with design considerations, channels can have varied paths, varied width, varied cross-sectional geometries, varied heights, and be composed of varied materials. In one embodiment, the channel can be a plurality of folded switch-backs which are serpentine. An example of a switch-back design is illustrated in FIG. 2. As shown in FIG. 2, a channel 12 is arranged in a continuous switch-back design. The figure additionally illustrates optional in-line heaters 14, algae removal system 16, and pumps or paddle wheels 18 along the path of the channel. The algae removal system can be equipped with or include an algae skimmer and can be configured for selective removal of a certain amount or a certain location of algae. Alternatively, the water containing the algae may be directed to an external filter or centrifugation system. The paddle wheels and/or pumps can be configured to provide a continuous flow of the water including algae. Such water flow direction is indicated by the arrows. Heaters can be utilized to maintain or alter the water temperature as desired for algae cultivation. Suitable heaters can include, but are not limited to, heat exchangers, electrical heaters, or the like. The heaters can be oriented along walls of the channel, suspended in-line, or in any location which can effectively and safely (i.e. without substantially damaging algae) control heat flow into the algae-laden water.

Switch-back designs can allow for more efficient use of land-area allotted to the system. A switch-back system can be further improved by increasing and further maximizing the length of the long sections of channels prior to curving back. Other channel configurations can include, but are not limited to, a series of straight channels, spiral channels, and the like. Furthermore, the channel system can, in one aspect, be connected in a manner to provide a continuous endless path, e.g. a raceway, switch-back, loop, or the like. Alternatively, the channel can be a specific length, with distinct endpoints. In the second arrangement, a channel can be, for example, a straight length of channel. The channel walls can be formed of any suitable material which provides sufficient mechanical strength to retain the algae-laden fluids and prevents undesirable degree of leaching from or ingress into the channel volume. Non-limiting examples of materials that can be used for the creation of channels includes concrete, plastic, fiberglass, composites of these materials, and combinations of these materials. In some embodiments, a porous material can be lined with a non-porous lining to form walls of the channel. For example, trenches can be dug into the earth and then lined with a suitable material. Alternatively, the trenches can be built above-ground such as by pouring concrete or plastic forms. The present system also allows for the use of clear pipes in place of the trough and cover, but pipes or tubes would be considerably more expensive and would only be justified in special circumstances. Thus, a channel may be created from the lower portion of a pipe or tube, and a cover may be created from the upper portion of a pipe or tube.

The algae to be used in production of specific products, such as fuel production, typically are capable of photosynthesis-that is, they use energy from sunlight. Therefore, when algae are growing photosynthetically they need to be exposed to sunlight. However, the mechanisms of photosynthesis can only use a portion of the light available. Too much light can actually cause damage to the organism. In addition, when algae are growing rapidly they will quickly fill the water in which they are growing, and the density of algae may begin to block the light from penetrating deeply into the water. In addition, water itself absorbs sunlight. For all these reasons, the depth of the water in the growth system can be altered to better encourage and sustain growth.

Experience indicates that the optimum depth of water for growing desired species of fuel-producing algae is between about 10 cm and about 30 cm. In one specific embodiment, the depth can be configured to be around 20 cm. In still another embodiment, the channel can be designed for a maximum water depth of about 30 cm, with the desired water level less than the maximum. The depth of the channel, combined with the amount of algae cultivated therein, can be selected to optionally shade algae near the bottom of the channel by a dense upper algae population near the top of the water volume. In this manner, a hybrid or combined two stage growth can be accomplished by selecting conditions to create such a bi-layer of algae, i.e. dark lower volume and a light upper volume which acts to at least partially block light from the lower volume. In one aspect, the water can be disturbed sufficiently to effectively circulate the algae, such as with aeration and/or circulation, such that cells are exposed to sunlight at the top, but do not remain in the intense sunlight for time periods sufficient to damage the algae.

The growth system can optionally lift or mix the water and algae in the trough, thus exposing the algae to greater amounts of light and allowing for greater amounts of algae in the system. To achieve the high surface area as inexpensively as possible, the channel can be fairly wide but not so wide as to inhibit mixing or make construction difficult. In one aspect, the channel can have a width of about 1 m to about 3 m, although other widths can also be suitable.

The channel material can be both tough and inexpensive. As mentioned previously, non-limiting examples of materials which can be used for the channel include concrete, plastic and fiberglass. The bed for the channel material can preferably be substantially flat and level in order to improve controllability of flow and efficient use of channel volumes. Formation of uniform and consistent channels can be achieved fairly simply with laser and computer-guided construction equipment. Once the bed has been prepared, the channel can be built either from preformed sections or can be built in place, either by slip-form construction or by similar processes. A method of continuous construction of plastic liner can be used, which works by placing a fabric in the bed of the trough and mixing plastic components which are machine-applied to the fabric and then cure to a smooth and continuous form. This method has been demonstrated at rates of up to 2,000 m$^2$ per day.

Figure 3:
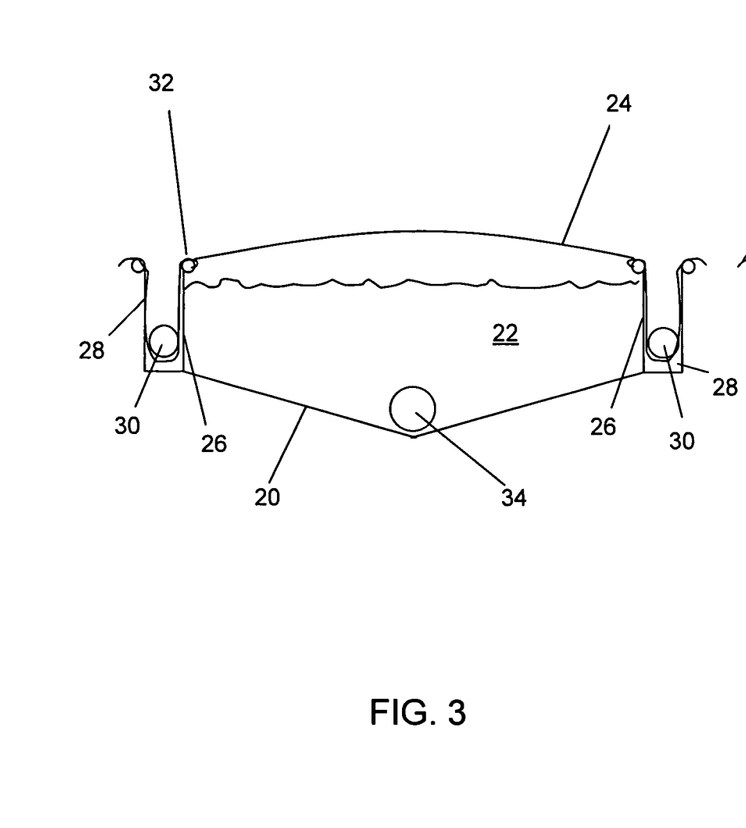
FIG. 3 is a cross-section view of a channel system in accordance with another embodiment of the present invention.

The channel can be light in color, e.g. white, so that sunlight is reflected back from the sides and/or bottom and illuminates algae from the sides and bottom of the trough. Such configuration increases utilization of the light energy introduced into the system. The bottom and/or sides can have a smooth and flat texture in this construction. The cross-sectional shape of the channel can vary depending on design preferences, construction constraints, and other system parameters. In one aspect, the bottom and/or sides can be slanted. In another aspect, the bottom of the channel can be substantially flat, or can alternatively slant to a point. A channel having a flat bottom is illustrated in FIG. 1, whereas a channel having a bottom that slants to a "V" is illustrated in FIG. 3. In one aspect, as in FIG. 3, the channel 20 can have a sloped contour forming a longitudinal depression along a length of the channel that is lower than surrounding portions of an inner wall of the channel. The bottom of the channel can have sides that slant and/or curve to form a smaller or larger flat bottom. Similarly, the side walls of the channel can be vertical, slanted, curved, or any other configuration useful in the cultivation of algae.

As with the channel, multiple designs for the cover are contemplated. In one aspect, a cover system including multiple covers can be utilized. In one aspect of the cover system, the cover system can include a first cover and a second cover, where the covers are distinguished by differences in translucence. For convenience in explanation, a first cover will have a greater translucence than a second cover. In algae growth utilizing staged growth dependant on light or darkness, the first cover can be placed above a first area of channel, and the second cover can be placed over a second, separate, area of channel, wherein the two channels can be optionally connected. Alternatively, the transition from the first cover to the second cover can be a smooth transition with a cover designed to change translucence from the first cover's translucence to the second cover's translucence, either in a step-wise manner or in a smooth transition along the length of the transition area. In still another embodiment, the second cover can be designed to removably cover the first cover and the channel. In this embodiment, the lighting conditions of the protected growth volume inside the channel can be altered by the presence or absence of the second cover. Such design does not require removal or bulk movement of the water and algae, although such removal could be used.

Figure 4:
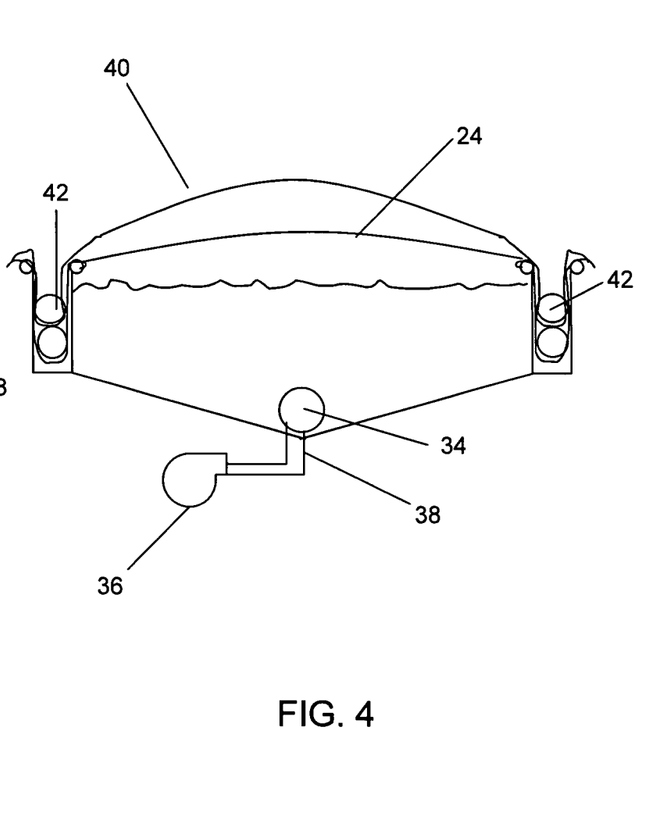
FIG. 4 is a cross-section view of a channel system in accordance with another embodiment of the present invention.

A cover system is illustrated in FIG. 3, wherein the channel 20 contains water including algae 22 and is covered by a first cover 24, i.e. a translucent cover. The cover passes over the side walls 26 of the channel and into smaller recessed or pocket channels 28 flanking the sides of the channel. The cover is held in place by a complementary retainer 30 that is of a size and weight to exert a force on the cover sufficient to form at least a partial seal 32 between the channel and the cover. The complementary retainer can be a rod or other long, high aspect ratio member sized to fit within the recessed channels. The translucent cover can be a flexible plastic cover which can be secured to the channel by a suitable securing mechanism. In the illustrated embodiment, the securing mechanism consists of a single or multiple sections of pipe 30 that exert a downward force on the plastic cover within the pocket channels 28 sufficient to form a seal 32. A resulting positive pressure in the growth volume can produce an inflated cover 24 that rises over the water 22 in the channel. Algae can be exposed to light and thus experience a light, growth stage while under the first cover. FIG. 3 also illustrates an aeration pipe 34 situated along the bottom of the channel at a lowest point of the sloped contour forming a longitudinal depression. In this case, it is placed in the middle of the channel and along the center of the bottom surface. The aeration pipe can be operatively connected to a pump (36 as illustrated in FIG. 4, and attaching piping 38 also in FIG. 4) and used to release or inject gas into the water. Such gas can aerate the water, as well as introduce a positive pressure into the system. The gas can include air or carbon dioxide, optionally filtered, and may be heated or cooled as needed to optimize growth conditions. During autotrophic or light stage growth, airflow can provide carbon dioxide to growing algae and remove oxygen from the water. In heterotrophic or dark stage growth, airflow can provide oxygen. Beyond heating or cooling the gas prior to injection, the flow rate of the gas can affect the temperature. Evaporation increases or decreases with airflow, and such should be taken into account when optimizing system parameters. Additionally, aeration provides lifting or agitation and rotation of algae between top and bottom of the trough. In one aspect, the aerating can vertically circulate the body of water along substantially an entire depth of the body of water. As such, mass circulation of the water and algae may optionally be used, however is not required, for effective algae cultivation.

Optionally, a second cover 40 can be placed above the first cover 24 as illustrated in FIG. 4. As noted previously, FIG. 4 illustrates a pump 36 attached through pipes 38 to the aeration pipe 34. Suitable pumps and associated fluid connections can be provided in any of the embodiments described herein. The second cover can have a lower translucence than the first cover and can optionally be opaque or substantially opaque. As illustrated, the second cover is situated above the first cover 24 and is held in place by a securing mechanism 42 similar to that used with the first cover. However, other securing mechanisms can also be used including, but not limited to, hooks, Velcro®, snaps, dead-weights, etc.

In an alternate embodiment, the water with the algae can be circulated through a first length of channel covered by a first cover, and subsequently circulated through a second length of channel covered by a second cover, wherein the first cover has a greater translucence than the second cover. In this case, the first and second covers are substantially static and need not be moved in order to provide varying growth environments to the algae. Such arrangement promotes multi-stage growth, where the first stage is autotrophic, or light growth stage, and the second is heterotrophic or dark stage growth. Autotrophic growth can be used to maximize the number of algae cells, whereas heterotrophic growth can be used to slow or stop the increasing cell number or size, and cause the algae cells to grow in other ways, such as, e.g. oil production.

In an embodiment, the first and/or second covers can be flexible. In a further embodiment, the flexible cover can be plastic. One configuration includes a loose-fitting flexible cover which stretches or extends across the channel. Under positive pressure, the loose-fitting cover creates a dome. Regardless of the flexibility of the cover, the covers can span the width of one or more channels. In a further embodiment, the covers can be disposable, meaning they can be made of materials that are configured for a limited number of uses, as based on product design, cost of materials, etc. As discussed, a first cover can be translucent, and a second cover can be opaque or substantially opaque. In an alternate embodiment, the second cover can be reflective, which can be used for temperature control. Optionally, the second cover can be slightly translucent, allowing a limited amount of light through, which would provide a simultaneous combination of autotrophic and heterotrophic growth.

The covers can be formed of any suitable material such as, but not limited to, polyethylene films, vinyl film, cellophane, polyethylene terephthalate, polypropylene, polyvinylidene chloride, ethylene vinyl alcohol, nylon, ethylene vinyl acetate, ant the like. Plastic film can be readily attached to the channel with a tight seal. The cover can either be stretched across the channel, or can be loose-fitting and inflated to form a dome above the channel. The inflation would take place by air or gas pumped into the algae growth environment. In the case of pipes or tubes, no separate cover is needed.

The cover material can be optionally joined to the channel along the edges of the channel. The attachment can be made with an adhesive such as glue, or in the case of a plastic-to-plastic seal, can be done ultrasonically, with heat, or with solvents. It is also possible to form a small gutter or other form along edges of the channels into which the cover material can be pushed and held either by its own compression or by a channel seal as described previously.

In one embodiment, the cover can be attached to the channel through ultrasonic welding or a thermal seal. In the case of a plastic film cover, the application can be a continuous process, wherein the cover is placed along the channel and the sealing mechanism is directed along the length and edges of the channel. Such process may be further enhanced with a pre-heating mechanism or other pre-treating process. A plastic film cover can be applied to be taut along the width of the channel. Alternatively, the film cover can be attached to the channel so as to be loose. When the positive pressure is introduced into the system, the film cover will inflate and create a dome cover.

The cover may also be perforated with holes or slits of appropriate dimension and spacing. These perforations can serve to allow venting of excess gas in the system, as well as controlled transpiration or evaporation of water. Transpiration allows removal of oxygen during active photosynthesis, and evaporation of water vapor allows cooling during high temperatures. The exact size and spacing of the openings can depend on the growing conditions and other variables, such as the amount of gas injected into the system. Holes or slits, therefore, can be placed at regular intervals throughout the system, or can be strategically placed along the length of the system as needed, depending on the configuration of the system. Covers can generally be attached so as to cover a single channel. Alternatively, covers can be attached to cover multiple channels, or even an entire system.

The cover material can be designed so as to be removable and replaceable. Such design can allow for ease in replacing damaged or worn covers, and/or can allow for changing of the cover for altering the parameters of the closed system, or in response to external environmental conditions.

The cover material can be translucent for photosynthetic (autotrophic) growth. For heterotrophic growth, as may be useful in some situations, it may be desirable to reduce or eliminate sunlight to encourage production of oil or starch. For this condition, the cover material can be opaque or substantially opaque. In an operational system, algae may be shunted or transferred from one channel to another to make the transfer from autotrophic (translucent cover) to heterotrophic (opaque cover). Alternatively, the covering of the channels could be altered, either through a progressive design element, or by manually removing and replacing the cover, or by placing one cover on top of another cover. Heterotrophic growth can also be encouraged by introducing materials into the system. Such materials may include biologically or genetically engineered materials.

To achieve uniform exposure of the algae to sunlight, to provide uniformity of nutrients, salinity, pH, and temperature, and to allow efficient harvesting, the water containing the algae can circulate in the channel and/or can be aerated. Circulation should be efficient but not so vigorous as to damage the algae or require excessive energy for circulation.

The simplest mechanism to achieve these objectives in a serpentine system is a low-cost paddle-wheel system driven by electric motors which gently but positively circulates the water in the channel. Circulation rates between 15 cm/s (centimeters/second) and 30 cm/s appear optimal, although other rates may be found suitable. In general, 15 cm/s is sufficient and uses the least energy. In a pipe/tube system, a simple pump using an Archimedes screw or other pumping mechanism would accomplish the same objective. Pumps could also be used in the channel system to circulate water. In the closed-channel system, the aeration pipes provide a lifting and circulation of the algae in the trough.

Control of water temperature in the growth channels is useful for several reasons: (1) growth can be optimized for many desirable species of algae by keeping the growth medium (water) between about 15° C. and about 35° C., and further optimally between about 20° C. and about 30° C.; (2) water temperature will affect which species of algae will become dominant, with the desired species having a specific water temperature; and (3) seasonal variations will affect the water temperature naturally unless some method of control is provided.

For these reasons the water can be warmed in the winter, and possibly cooled in the summer if transpiration or evaporation through the cover is not sufficient to maintain the desired water temperature in the summer. Temperature control can be provided by installing heat transfer plates in the channel or pipe. Such heat transfer devices can be supplied with either heated or cooled transfer fluid depending on the temperature change desired. In a closed-trough system, temperature may be controlled by heating or cooling the aeration gas pumped through the aeration pipe in the bottom of the trough.

Gas can be injected into the water in the troughs or pipes for at least four reasons: (1) to provide carbon dioxide as a growth nutrient in autotrophic growth; (2) to remove oxygen during autotrophic growth; (3) to provide oxygen during heterotrophic growth; and (4) to provide sufficient gas flow to increase evaporation of water for cooling in the summer. Carbon dioxide injected into the water may be obtained either by injecting air (containing carbon dioxide), or by injecting more concentrated carbon dioxide from fermentation or other sources. If air is used as a carbon dioxide source, the air can be filtered with filters of sufficiently small size to prevent the entry of wild algae or algae predator spores or cells into the water. In either case, the injection system can force pressurized gas into the water flow through nozzles positioned in the direction of flow of the water.

In one aspect, the system can include a water inlet wherein water may be added to the system. Such water addition can be used to initially charge the system, or can be performed periodically or continuously to maintain a certain minimum water level. As with gas injection, the water can be filtered or otherwise purified, preferably to remove contaminants and undesired strains of algae which could affect algae growth.

Nutrients other than carbon dioxide may be injected in a similar manner to the carbon dioxide, whether in liquid or gaseous form. An example of a nutrient to be added is bioavailable nitrogen, which can be added in a fast-growth autotrophic stage and withheld in an oil-producing heterotrophic stage of algae growth. Additional nutrients may include sugar, silica, magnesium, potassium, phosphorus, and compounds containing these substances.

Depending on the species of algae, it may also be important to maintain a specific salinity and pH of the water. Such control may be accomplished by adding salt or adding water to the system, or by similarly adding or diluting chemicals used to maintain the pH.

The same injectors may be used to insert other substances which may be needed, such as chemicals to prevent disease or predatory growths. Other substances which may be injected include biological materials to encourage the growth of oil or starch in the algae.

Mature algae may be collected or harvested by various means. Two non-limiting examples include skimming from the top of the water, and harvesting all algae together at the same time. The first method provides a continuous flow, while the latter is simpler in operation, but produces a batch process. For the first method, a skimmer is inserted into the water flow. This may be either in the form of a sluice for passive operation, or in the form of a paddle wheel for active operation. Both mechanisms are equipped with an adjustment for depth to set the desired degree of skimming. Alternatively, algae may be separated by filtration or centrifugation, in either a batch or continuous mode. The water may then be returned to the growth channels for re-use.

The system can be fitted with openings to add new algae into the system, as needed. These can be designed to minimize the entry of unwanted atmosphere or contaminants into the system.

Periodically, it may be necessary to clean the system and destroy any unwanted growths which may have unintentionally entered the system (i.e. lyse the system). This may be accomplished either chemically (e.g. chlorine or copper sulfate added to cleaning water), or thermally (e.g. hot water or steam cleaning). In either case, the materials used in the trough or pipe construction can be designed to be capable of withstanding the cleaning method used. An injection method can be supplied to introduce the desired cleaning agent into the system.

In conclusion, the methods and systems presented herein provide novel means to ensure that desired species of algae can be grown in a controlled and highly productive way to maximize the production of desired oils, starches, or biomass.

The following examples present various methods for making algae growth environments of the present invention. Such examples are illustrative only, and no limitation on present invention is meant thereby.

EXAMPLES

Example 1

Each growth system is constructed of either a single long trough arranged in a serpentine configuration or from individual troughs arranged in a regular pattern but not connected in a serpentine arrangement. Each trough is fitted with a flexible plastic cover inflated to form a flattened dome. The system of troughs covers an area of one hectare, and multiple systems may be laid out on available land to fill it as completely as possible.

The trough is two meters in width, so the total length for an area of one hectare is 5,000 m. Each individual run is 100 m long, with 50 runs parallel to each other to form a system which is approximately square with dimensions of 100 m by 100 m (thus giving 10,000 $m^2$ or one hectare of trough area).

The trough is formed by first, precisely leveling a one-hectare area of ground, then forming a channel in the ground two meters wide and 30 cm deep with a small separation between adjacent channels sufficient only to allow passage by foot or for the wheels of a tractor spanning the trough. (Because of the separation between adjacent channels the total system is not quite square). The depth is substantially constant throughout the entire system.

After the shape of the trough is formed in the earth, the trough lining is formed in place by a machine. The trough-lining machine is of known construction, which spans the trough and follows its length to create a plastic lining. The machine first unrolls a woven material and presses it down to line the earth in the shape of the trough. The machine then applies a mix of plastic-forming materials from onboard tanks onto the woven material and smoothes this mixture into the final shape of the trough. The mixture contains a catalyst which quickly hardens the plastic into the finished lining. The finished trough is essentially rectangular with a flat bottom, straight sides, and a lip which extends outward from the top of the vertical sides to provide an attachment point for the cover. The plastic material is light-colored, essentially white.

A second similar machine then follows along as soon as the trough is hardened and unrolls a clear polyethylene or polycarbonate film with dimensions somewhat wider than the trough. This machine has sealing rollers that apply a glue and press the cover sheet to the lip of the trough. The seal can be optionally subjected to heating, ultrasound, or other treatments to improve bonding. If the growth system is intended for dark-stage or heterotrophic growth, the plastic cover is dark, essentially opaque.

Once the lined trough is constructed, it is equipped with the required operating machinery. If arranged as a serpentine, then after each turn in the serpentine a paddle wheel is situated to provide water movement down the run, for a total of 50 paddle wheels. Similarly, the system has 50 injector nozzles for gases and nutrient injection, and 50 thermal transfer plates for heating and optionally cooling, with one transfer plate assembly after each paddle wheel where circulation over the plate is optimal. If the system is a collection of individual troughs, each trough is equipped with an aeration pipe in the bottom to lift and circulate the algae and provide aeration.

At the end of the system is a diverter which can direct the algae-laden water into either a harvesting system or into another growth system configured for dark-stage or heterotrophic growth. Alternatively, the water may be diverted back to the beginning of the serpentine to continue circulating until the desired growth has been achieved.

Example 2

In the foregoing one-hectare system, the covered trough is now ready for the introduction of the water, nutrients, and algae needed for growth. Water is supplied from holding tanks where it has been filtered and treated to remove unwanted algae and other organisms, and brought to approximately the desired temperature. Sufficient water is added to bring the depth in the entire system to approximately 22 cm, somewhat below the top of the 30 cm depth of the trough. When in operation, additional water will be added by the same means to maintain this depth.

The cover is inflated and positive pressure is maintained in the system thereafter, keeping the cover lifted into a flattened dome. All air or gases injected into the system are filtered to prevent intrusion of unwanted organisms. Filtered nutrients are added through injector nozzles to achieve the optimal balance for growth, and the algae are then added. The circulation paddles will keep the combination of water, nutrients, and algae mixed and moving continuously at a rate of approximately 15 cm/s. Temperature is maintained by transpiration and evaporation through the slots in the cover sheet, or alternatively by supplying heated or cooled thermal transfer liquid to the thermal transfer plates in the troughs.

Example 3

Optimal growth may be achieved by a mixture of blue-green algae (cyanobacteria) such as *Synechococcus*, with a green algae such as *Chlorella*. The *Synechococcus* fixes nitrogen (making it bio-available) from atmospheric $N_2$ dissolved in the water, thus reducing costs by avoiding the need for externally-supplied and relatively expensive synthetic nitrogen fertilizer. In addition, its genome has been sequenced. The advantage of *Chlorella* is that it is cultivated widely and is well-known and its genome is being sequenced. For *Synechococcus* a strain will be used which will thrive at app. 35° C., which is a good temperature for either *Chlorella*, and will be the temperature of the entire system.

The most important nutrients are carbon and nitrogen. If the system is intended for light-stage (autotrophic or photosynthetic) growth, the carbon will come from carbon dioxide either from the atmosphere or from an external source, and bio-available nitrogen from either blue-green algae or from an external source. If the system is intended for dark-stage (heterotrophic) growth, the carbon will come from sugars supplied to the system or from carbon dioxide added to the system. Nitrogen may be limited in heterotrophic systems to stimulate the production of lipids by the algae.

Of course, it is to be understood that the above-described arrangements are only illustrative of the application of the principles of the present invention. Numerous modifications and alternative arrangements may be devised by those skilled in the art without departing from the spirit and scope of the present invention and the appended claims are intended to cover such modifications and arrangements. Thus, while the present invention has been described above with particularity and detail in connection with what is presently deemed to be the most practical and preferred embodiments of the invention, it will be apparent to those of ordinary skill in the art that numerous modifications, including, but not limited to, variations in size, materials, shape, form, function and manner of operation, assembly and use may be made without departing from the principles and concepts set forth herein.

What is claimed is:

1. A system for cultivating algae, comprising:
   a channel with a cover system that substantially closes the channel to an outside environment and forms a protected growth volume, the cover system being designed to selectively adjust amounts of light allowed to enter the protected growth volume and the channel being formed in the earth;
   a body of water including one or more algae contained in the channel; and
   a gas pump configured to introduce a positive pressure into the protected growth volume.

2. The system of claim 1, wherein the cover system includes a first cover and a second cover, such that the first cover has a greater translucence than the second cover.

3. The system of claim 2, wherein the first cover and the second cover are configured to cover different portions of the channel.

4. The system of claim 2, wherein the second cover is configured to removably cover at least a portion of the channel and the first cover.

5. The system of claim 2, wherein at least a portion of the second cover is opaque or substantially opaque sufficient to block light to promote heterotrophic growth of the algae.

6. The system of claim 2, wherein at least one of the first and second covers includes perforations.

7. The system of claim 1, further comprising a reflecting layer on a portion of an inner wall of the channel within the protected growth volume, said reflecting layer oriented to redirect light through the protected growth volume.

8. The system of claim 1, wherein at least a portion of the cover system includes a flexible plastic material.

9. The system of claim 1, wherein the system is substantially closed and the body of water circulates through the system.

10. The system of claim 1, wherein the system is substantially closed and the body of water is aerated.

11. The system of claim 1, wherein the channel has a sloped contour forming a longitudinal depression along a length of the channel which is lower than surrounding portions of an inner wall of the channel.

12. The system of claim 11, further comprising an aeration pipe oriented along at least a portion of the longitudinal depression and operatively connected to the gas pump.

13. The system of claim 1, further comprising a securing mechanism to retain the cover system over the channel, said securing mechanism including recessed channels along opposing upper edges of the channel and at least one elongated member shaped to fit into the recessed channels sufficient to retain a flexible cover lying in the recessed channels.

14. A multi-stage method of cultivating algae, comprising providing a body of water in a substantially enclosed system including a length of channel, a first cover, and a second cover, wherein the length of channel is formed in the earth, at least one of the first cover and second cover contributes to the substantially enclosed system and the first cover has a greater translucence than the second cover; and
cultivating said algae within the body of water under conditions sufficient to promote growth of algae, wherein the growth includes a light growth stage and a dark growth stage, said dark growth stage being a function of the second cover being oriented over the body of water.

15. The method of claim 14, further comprising circulating the body of water through the enclosed system under positive pressure conditions sufficient to prevent ingress of external atmosphere or material.

16. The method of claim 14, wherein the body of water is circulated through a first length of the channel covered by the first cover and subsequently circulated through a second length of the channel covered by the second cover.

17. The method of claim 14, further comprising aerating the body of water by injecting a gas into the body of water to vertically circulate the body of water along substantially an entire depth of the body of water.

18. The method of claim 14, wherein the cultivating said algae includes exposing the algae to light through the first cover to induce the light growth stage and subsequently covering the first cover with the second cover to induce the dark growth stage.

19. The method of claim 14, wherein the conditions for growth of the algae are selected and maintained to promote selective growth of the algae over undesired strains of algae.

20. The method of claim 14, further comprising forming the enclosed system by steps including:
   forming the length of channel in the earth;
   lining the channel sufficient to reduce or prevent migration of materials between the channel and surrounding earth;
   covering at least a portion of the channel with the first cover, where the first cover is a plastic sheet having perforations therein; and
   securing the first cover sufficient to form a seal with the channel.

21. The method of claim 20, wherein the channel is formed in a continuous endless pathway.

22. A system for cultivating algae, comprising:
   a plurality of individual channels being formed in the earth and lined at least partially to prevent migration of materials between the individual channels and surrounding earth, and including a reflecting layer on a portion of an inner wall of the individual channels, said reflecting layer being oriented to redirect light through a central portion of the individual channels, and said channels having slanting inner walls approaching each other near a bottom of the channel to form a longitudinal depression along the length of the channels;
   a first cover that substantially closes the channels to an outside environment and forms a protected growth volume, said first cover being substantially translucent and being formed of a thin layer of plastic having a plurality of perforations;
   a second cover configured to at least partially cover the first cover, said second cover being substantially opaque and being formed of a thin layer of plastic having a plurality of perforations;

two pocket channels flanking opposing edges of either each of the individual channels or the plurality of individual channels, said pocket channels configured to retain the first cover held in place by a complimentary retainer, said complimentary retainer being of sufficient size and weight to at least partially fit in the two pocket channels to produce at least a partial seal between the first cover and the individual channels;

a body of water including preselected strains of algae contained in the individual channels;

a gas pump operatively connected to the protected growth volume and configured to introduce a positive pressure into the protected growth volume; and a gas distributor operatively connected to the gas pump and oriented to release gas along a bottom region of the individual channels sufficient to provide vertical mixing of the body of water.

\* \* \* \* \*